(12) United States Patent
Abe et al.

(10) Patent No.: US 6,679,106 B1
(45) Date of Patent: Jan. 20, 2004

(54) ROAD SURFACE ROUGHNESS MEASURING DEVICE

(75) Inventors: Hironari Abe, Kokubunji (JP); Toshio Sawa, Sayama (JP); Atsushi Kasahara, Sapporo (JP)

(73) Assignee: Nippo Sangyo Co., Ltd., Tokyo (JP)

( * ) Notice: Subject to any disclaimer, the term of this patent is extended or adjusted under 35 U.S.C. 154(b) by 0 days.

(21) Appl. No.: 09/926,772
(22) PCT Filed: Apr. 20, 2000
(86) PCT No.: PCT/JP00/02586
§ 371 (c)(1), (2), (4) Date: Mar. 18, 2002
(87) PCT Pub. No.: WO01/81861
PCT Pub. Date: Nov. 1, 2001

(51) Int. Cl.[7] ................................................. G01B 5/28
(52) U.S. Cl. .......................... 73/105; 73/104; 73/1.89
(58) Field of Search ............................... 73/105, 104, 9, 73/1.39

(56) References Cited

U.S. PATENT DOCUMENTS

| 4,712,418 | A | * | 12/1987 | Augustin | ........................ | 73/9 |
| 6,452,170 | B1 | * | 9/2002 | Zypman et al. | ............. | 250/306 |

FOREIGN PATENT DOCUMENTS

| JP | 05-087561 | A | * | 4/1993 | ........... G01B/21/30 |
| JP | 11-083471 | | * | 3/1999 | ........... G01B/21/30 |

* cited by examiner

*Primary Examiner*—Hezron Williams
*Assistant Examiner*—Charles Garber
(74) *Attorney, Agent, or Firm*—Westerman, Hattori; Daniels & Adrian, LLP

(57) ABSTRACT

The object of the present invention is to provide a road surface roughness measuring apparatus for measuring the coefficient of dynamic friction and the roughness of the road surface in each direction at a same section where the coefficient of dynamic friction is measured, said apparatus divides the measuring circle on the road surface into a plurality of sections, on which measuring circle the rotary type unit for measuring the coefficient of dynamic friction measures the coefficient of dynamic friction. The road surface roughness measuring apparatus has: a frame (32) having a plurality of legs (31) used for placing the apparatus on a road surface (G); a rotary shaft (45) mounted on the frame (32) and extending vertically; a rotary encoder (44) mounted on the top end of the rotary shaft (45); a rotation plate (50) mounted on the bottom end of the rotary shaft (45); a motor (39) provided with a speed reducing gear and for driving the rotary shaft via gears (41, 41*a*); and a laser displacement gauge (51) mounted on the rotation plate (50). The laser displacement gauge (51) is disposed in such a way as to measure a road surface roughness along a measuring circle (P) on which the rotary type unit for measuring the coefficient of dynamic friction measures the coefficient of dynamic friction by the rotation of the rotation plate. The measuring circle (P) is divided into a plurality of sections and the road surface roughness for each section (a to h) is calculated based on the signals of the laser displacement gauge (51) and the rotary encoder (44).

1 Claim, 5 Drawing Sheets

ROAD SURFACE ROUGHNESS MEASURING DEVICE

TECHNICAL FIELD

The present invention relates to a road surface roughness measuring apparatus for measuring the roughness of a road surface at the same position, wherein a rotary type unit for measuring the coefficient of dynamic friction measures the coefficient of dynamic friction of the road surface.

BACKGROUND TECHNICAL CONTENTS

There are many conventional technologies for measuring the coefficient of dynamic friction of the road surface. According to such conventional technologies, a measuring unit is pulled by a tractor and separately measures the roughness and the coefficient of dynamic friction of the road surface. However, in general, the measurement values of the coefficient of dynamic friction tend to produce errors depending upon the measuring units. In order to correct such errors in the measurement values of the coefficient of dynamic friction, usually, the relationship between the coefficient of dynamic friction and the roughness of the road surface is determined; and then, an international friction index (IFI) value is determined based on such relationship.

In order to determine the IFI value, it is necessary to measure the roughness and the coefficient of dynamic friction at the same position of the road surface. However, it was considerably difficult to measure the two values (the roughness and the coefficient of dynamic friction) at the same position of the road surface.

As to the measurement of the coefficient of dynamic friction, the applicant discloses technical contents relating to a rotation type device for measuring the coefficient of dynamic friction in Japanese Patent Application Publication No. 3-10062. However, such technical contents (disclosed in Japanese Patent Application Publication No. 3-10062) are used for measuring the coefficient of dynamic friction of the road surface in the shape of a circle. In other words, such technical contents are not used for measuring the roughness of the road surface. Accordingly, in order to determine the IFI value, another apparatus for measuring the roughness at the same position is necessary. Therefore, there has been desired an apparatus which is able to measure the road surface roughness and the coefficient of dynamic friction in detail at a plurality of sections on the same measuring path as the measuring circle of the rotation type device.

The present invention has been provided to solve the above-mentioned problem. The object of the present invention is to provide a road surface roughness measuring apparatus for measuring the coefficient of dynamic friction and the roughness of the road surface in each direction at a same section where the coefficient of dynamic friction is measured. The apparatus divides the measuring circle on the road surface into a plurality of sections, on which measuring circle the rotary type unit for measuring the coefficient of dynamic friction measures the coefficient of dynamic friction.

DISCLOSURE OF THE INVENTION

The present invention is a road surface roughness measuring apparatus being combined with a rotary type unit for measuring the coefficient of dynamic friction, which apparatus comprises: a frame having a plurality of legs provided for placing the apparatus on a road surface; a rotary shaft mounted on such the frame and extending in vertical direction; a rotary encoder mounted on the top end of such the rotary shaft; a rotation plate mounted on the bottom end of such the rotary shaft; a motor being combined with a speed reducing means and driving the rotary shaft via gears; and a laser displacement gauge mounted on the above-mentioned rotation plate.

The laser displacement gauge is disposed so as to measure by the rotation of the above-mentioned rotation plate along a measuring circle, on which circle the rotary type unit for measuring the coefficient of dynamic friction measures the coefficient of dynamic friction.

The apparatus has a function for dividing the measuring circle into a plurality of sections and a function for calculating the road surface roughness for each section based on the signals of the laser displacement gauge and the rotary encoder.

According to the road surface roughness measuring apparatus of the present invention, the apparatus is placed at the same position on the road surface, where the rotary type unit for measuring the coefficient of dynamic friction measures the coefficient of dynamic friction, is rotated along the same path on which path the rotary type unit for measuring the coefficient of dynamic friction measures the coefficient of dynamic friction, and measures the road surface roughness. The measurement of the road surface roughness is carried out by measuring the distance from the measuring circle to the laser displacement gauge, which is mounted on the rotation plate being rotated by the motor combined with the speed reducing means. The measurement of road surface roughness is carried out according to the sampling signal of the rotary encoder and calculating the roughness. Then, the measuring circle is divided into the plurality of sections and the road surface roughness is outputted as a mean profile depth (hereinafter referred to as a MPD) value, for example, for each divided section.

Therefore, it is possible to measure the roughness in the plural directions and the coefficient of dynamic friction at the same position; and thus, it is possible to carry out a more analytical research by the use of this more detailed road surface data.

In this connection, when carrying out the present invention, if the coefficient of dynamic friction is measured first, rubber and the like or water is attached to the road surface. Therefore, it is preferable that the roughness is measured first.

When carrying out the present invention, it is possible to measure the road surface roughness in the entire area within the measuring circle.

BEST MODE FOR CARRYING OUT THE INVENTION

In order to explain the present invention in detail, one embodiment in accordance with the present invention will be described hereinafter with reference to the drawings.

Figure 1:
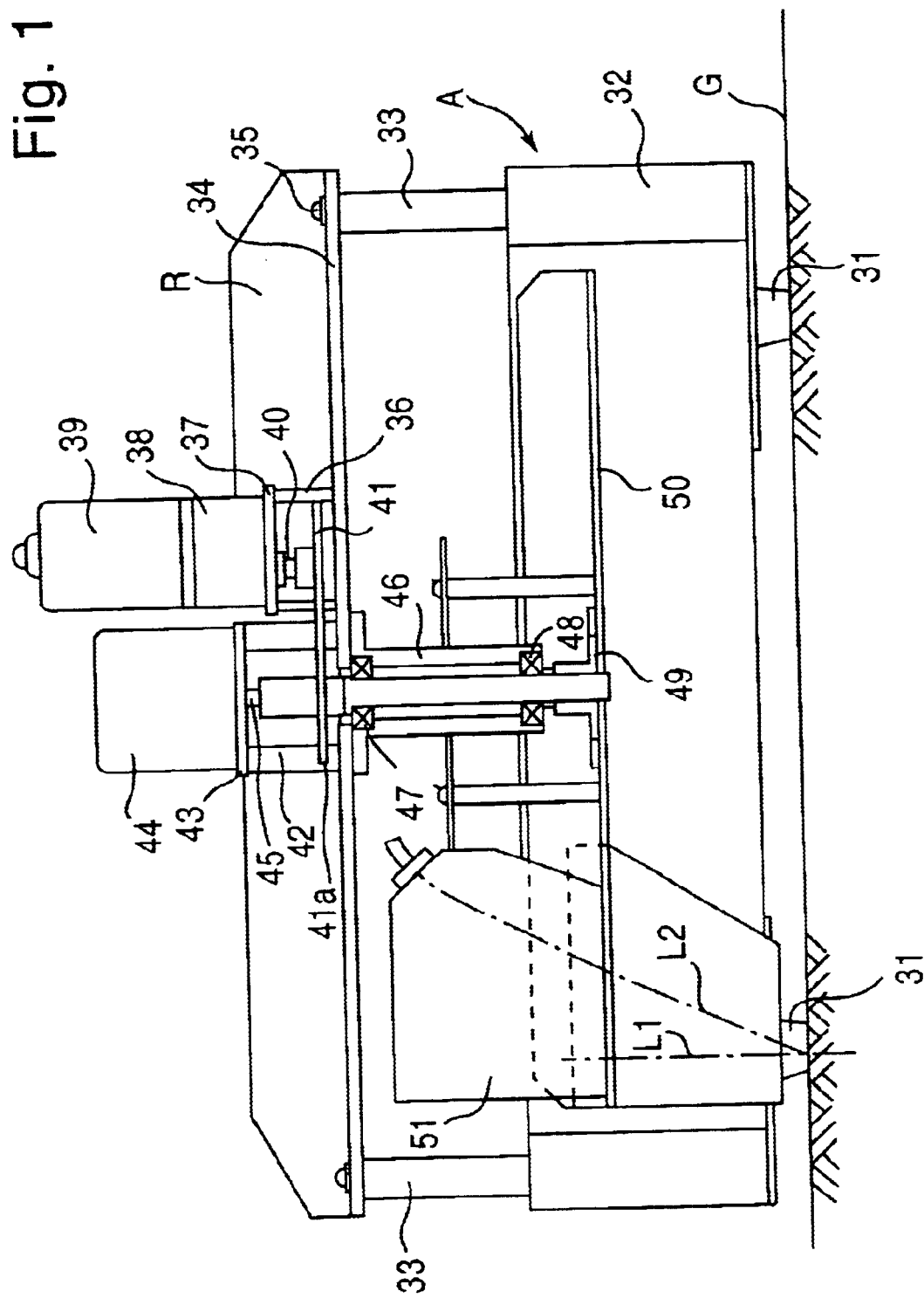
FIG. 1 is a side view showing one embodiment of a road surface roughness measuring apparatus in accordance with the present invention.
Figure 2:
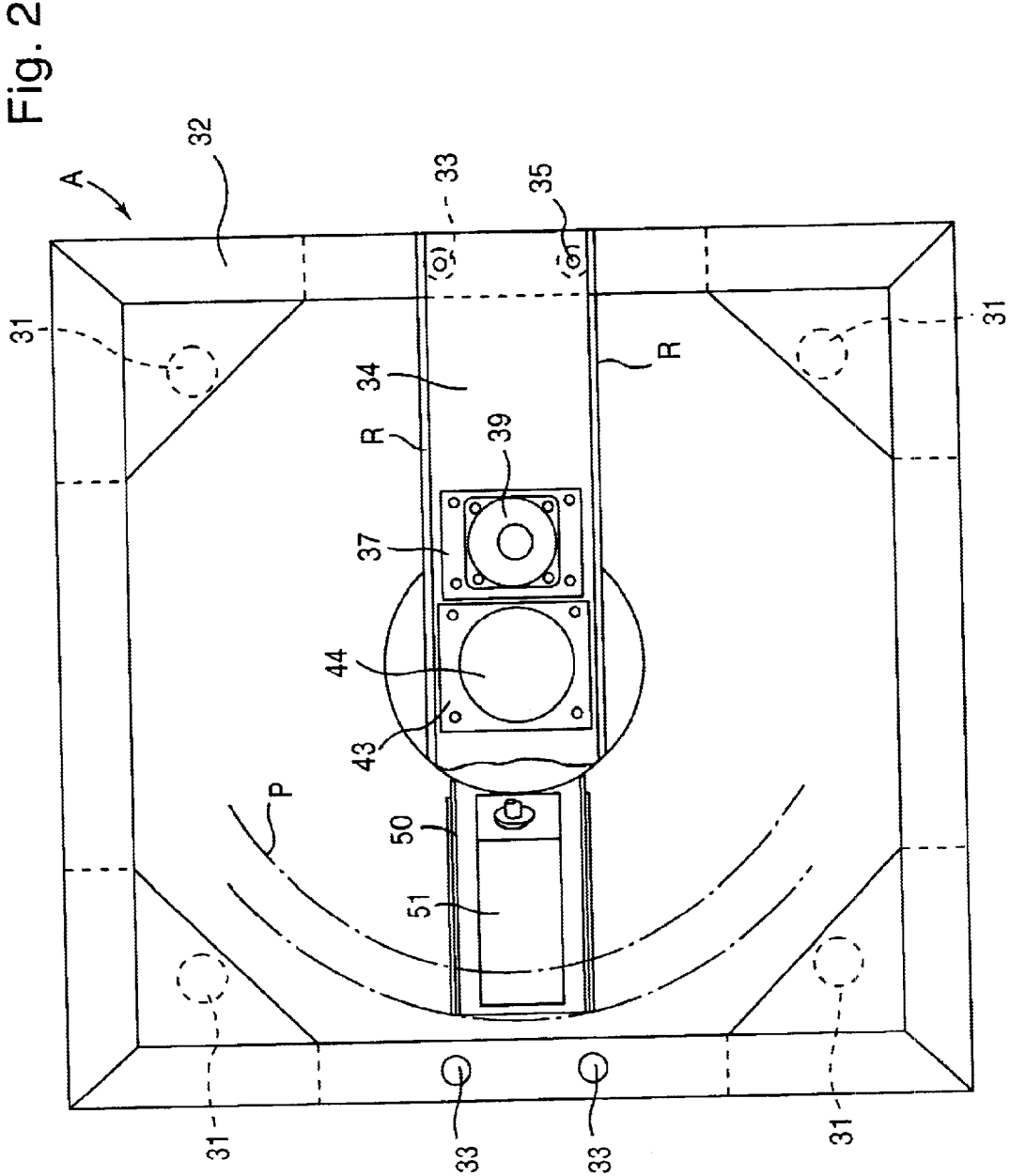
FIG. 2 is a plan view of FIG. 1.

In FIGS. 1 and 2, a road surface roughness measuring apparatus, which is generally indicated by a reference character A, includes a square frame 32 having on the bottom thereof a plurality of legs 31 (four legs in the drawing) made of an elastic material and used for placing the apparatus on a road surface G, support columns 33 disposed on the frame 32, and a support plate 34 whose both end portions are supported by the support columns 33 and fixed thereto by screws 35. Here, a reference character R designates a rib erected on both edge portions of the support plate 34.

The first base plate 37 is fixed to the support plate 34 via the first support legs 36 and a motor mounted with a speed reducing gear 38 is mounted on the first base plate 37. The speed reducing gear 38 has, for example, a speed reducing ratio of about 1/200 and an output shaft 40 is provided with the first gear 41.

The second base plate 43 is fixed in parallel to the support plate 34 via the second support legs 42 and a rotary encoder 44 is mounted on the base plate 43. The rotary shaft 45 of the rotary encoder 44 is provided with the second gear 41a engaged with the above-mentioned first gear 41 and the lower portion of the rotary shaft 45 is supported by bearings 47, 48 held by a bearing bracket 46 and the bottom end thereof is fixedly provided with a rotation plate 50.

The rotation plate 50 is provided with the laser head 51 of a laser displacement gage. The laser head 51 itself is a publicly known one, in which laser light L1 emitted by a light emitting device is reflected by the road surface G and part L2 of the reflected light is received by a light receiving device and a distance to the road surface G is determined by the light receiving position.

Further, a measuring circle P drawn on the road surface G by the laser light L1 emitted from the laser head 51 when the rotation plate 50 is rotated around the rotary shaft 45 is set in such a way as to agree with the position where a rotary type unit for measuring the coefficient of dynamic friction measures the coefficient of dynamic friction.

Figure 3:
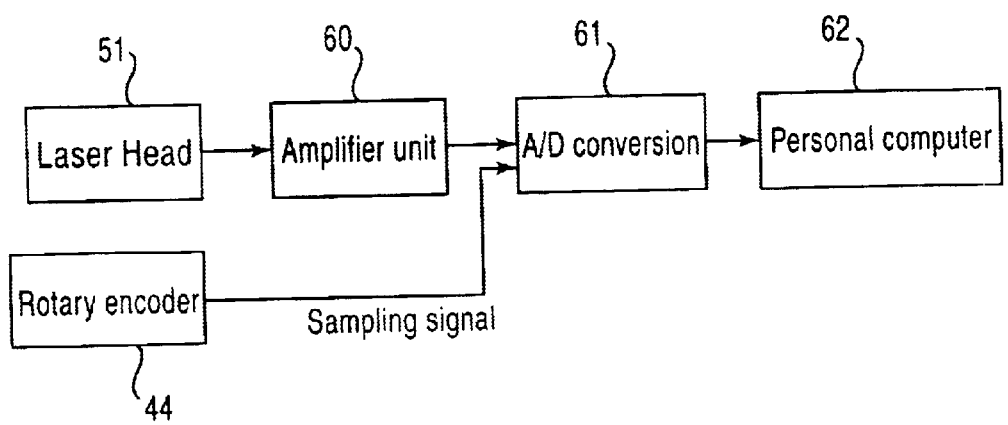
FIG. 3 is a block diagram of a road surface roughness measuring apparatus in accordance with the present invention.

On the other hand, in an electric circuit, as shown in FIG. 3, the output of the laser head 51 is connected to an A/D converter 61 via an amplifier unit 60 and the output of the rotary encoder 44 is also connected to the A/D converter 61 and then both are connected to a personal computer 62 from the A/D converter 61. Here, a battery (12 Volt) for a vehicle is used as a power source thereof.

Figure 5:
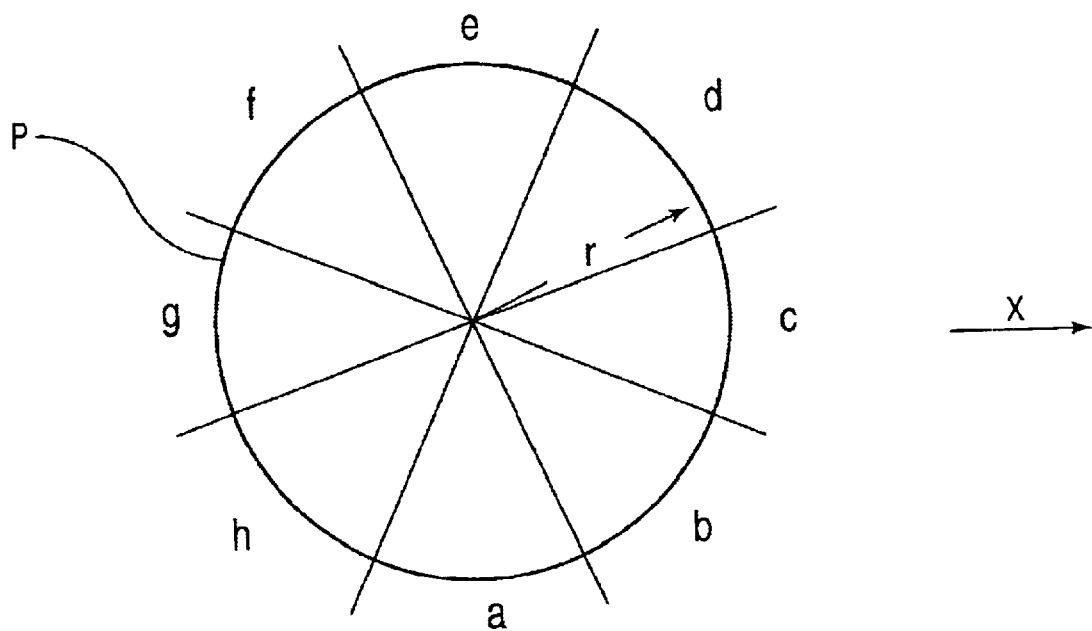
FIG. 5 is a drawing of the sections of a measuring circle.

As shown in FIG. 5, the circumference of the measuring circle P is divided into 8 sections and a mean profile depth (hereinafter referred to as MPD) is calculated for each section. For example, an MPD in the direction X of running is calculated from the average of points a and e, and an MPD in the direction perpendicular to the direction of running is calculated from the average of points c and g, and an MPD in the direction at 45 degrees to the direction of running is calculated from the average of points b and f and the average of points d and h, respectively. Of course, the whole MPD can be calculated from the average of all the points a to h.

The measurement of the road surface roughness by the road roughness measuring apparatus in accordance with the present invention is conducted before the measurement of the coefficient of dynamic friction. That is, first, the road surface roughness apparatus A is placed on the road to measure the roughness of the road surface; and then, the rotary type unit for measuring the coefficient of dynamic friction is placed at the same position and both the apparatus and the unit are rotated on the same path to measure the surface roughness and the coefficient of dynamic friction at the same position to calculate an IFI value from the roughness and the coefficient of dynamic friction of the road surface.

Figure 6:
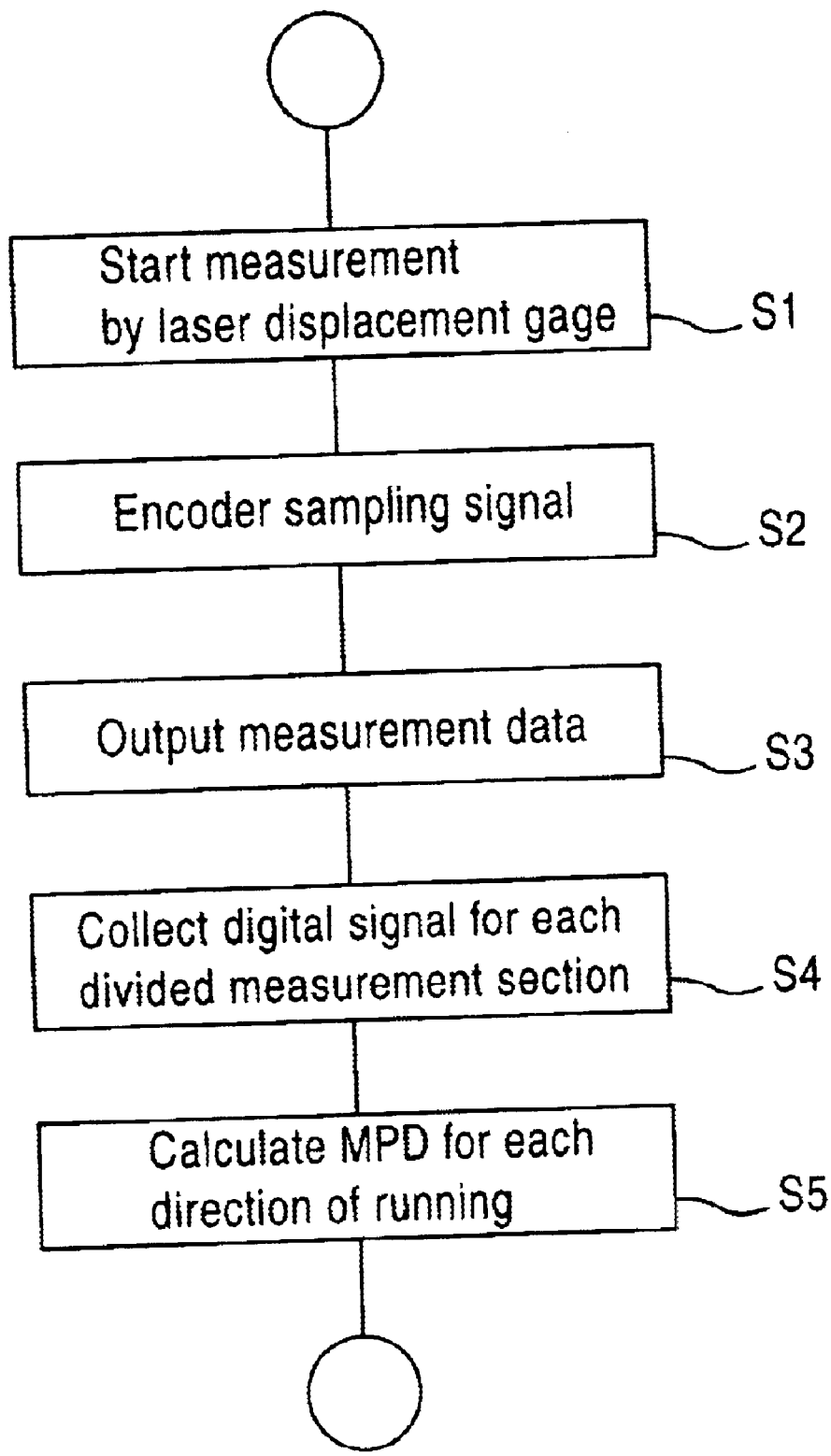
FIG. 6 is a flow chart for calculating an MPD in each direction of running.

In the measurement of the MPD in each direction, as shown in FIG. 6, in the step S1, the signal of the receiving device of the rotating laser head 51 is applied to the amplifier unit 60 and is converted into voltage proportional to a distance from the road surface and is applied to the A/D converter 61.

On the other hand, a sampling signal from the rotary encoder 44 is also applied to the A/D converter 61 (step S2) and the signal of the laser head 51 is sampled by the sampling signal and is outputted as a digital signal and is stored in the personal computer 62 (step S3).

Then, the digital signal is collected for each divided measurement section (step S4) and the personal computer 62 calculates an MPD designating the surface roughness for each section from the stored data (step S5) and the result of calculation MPD is outputted.

Figure 4:
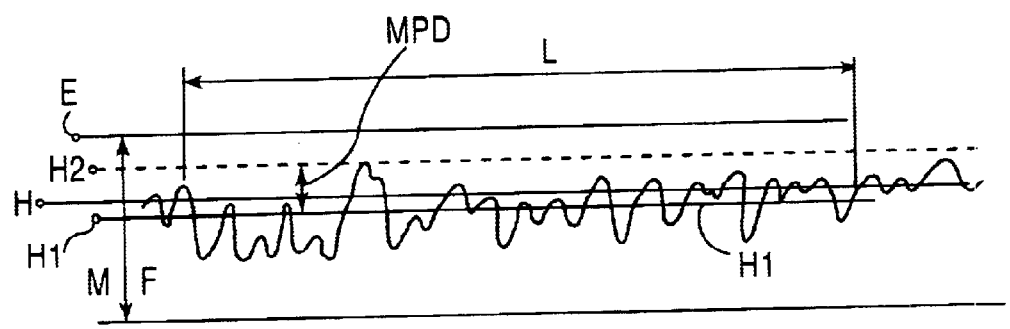
FIG. 4 is a drawing of one example of a road surface roughness being measured by the present invention.

FIG. 4 shows one example of the result. In FIG. 4, a lateral axis designates a length (length of arc of the measuring circle P) and a reference character L designates a sampling length. A vertical axis designates a distance from the laser head 51 and a reference character E designates the upper limit of the measuring range M of the laser head 51 and a reference character H designates the level of the road surface.

In this manner, the personal computer 62 calculates a regression straight line H1 from the value obtained by measuring the bumps and dips F of the road surface with respect to the sampling length L by the laser displacement gage and subtracts the regression straight line H1 from a level H2 of the maximum bump to calculate the MPD.

In this connection, the position H of the leg 31 is not in the measuring range M of the laser head 51 of the laser displacement gage so as to prevent the leg 31 from posing a barrier against measurement and making it impossible to measure all the bumps and dips of the road surface in the measuring range M of the laser head 51.

INDUSTRIAL FIELD

As described above, according to the present invention, in combination of the road surface roughness measuring apparatus and the rotary type unit for measuring the coefficient of dynamic friction, it is possible to measure the road surface roughness at the same position on the measuring circle in the plural directions with respect to the direction of running by one operation and to output the results of measurement to, for example, the personal computer. Therefore, it is possible to determine the IFI value of the road surface in detail from the measurement value of the coefficient of dynamic friction and that of the road surface roughness at the same position; and thus, to effectively use the IFI value for the research on the slip of the tire of an automobile or an airplane.

What is claimed is:

1. A road surface roughness measuring apparatus being combined with a rotary type unit for measuring the coefficient of dynamic friction, the apparatus comprising:

a frame having a plurality of legs provided for placing the apparatus on a road surface;

a rotary shaft mounted on the frame and extending in a vertical direction;

a rotary encoder mounted on the top end of the rotary shaft;

a rotation plate mounted on the bottom end of the rotary shaft;

a motor being combined with a speed reducing means and driving the rotary shaft via gears; and a laser displacement gauge mounted on the above-mentioned rotation plate, wherein:

the laser displacement gauge is disposed so as to measure by the rotation of the rotation plate along a measuring circle, on which circle the rotary type unit for measuring the coefficient of dynamic friction measures the coefficient of dynamic friction, and the apparatus has a function for dividing the measuring circle into a plurality of sections and a function for calculating the road surface roughness for each section based on the signals of the laser displacement gauge and the rotary encoder, so as to calculate a mean profile depth in the circumference of the measuring circle and each of mean profile depths in the direction of running, the direction perpendicular to the direction of running and the direction at 45 degrees to the direction of running, substantially at the same time.

* * * * *